US010332305B2

(12) United States Patent
Zhou et al.

(10) Patent No.: US 10,332,305 B2
(45) Date of Patent: Jun. 25, 2019

(54) CINEMATIC RENDERING OF UNFOLDED 3D VOLUMES

(71) Applicant: Siemens Healthcare GmbH, Erlangen (DE)

(72) Inventors: Shaohua Kevin Zhou, Plainsboro, NJ (US); Klaus Engel, Nürnberg (DE); Andreas Wimmer, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 216 days.

(21) Appl. No.: 15/061,188

(22) Filed: Mar. 4, 2016

(65) Prior Publication Data

US 2017/0256090 A1    Sep. 7, 2017

(51) Int. Cl.
*G06T 15/08* (2011.01)
*G06T 17/00* (2006.01)
*G06Q 50/22* (2018.01)

(52) U.S. Cl.
CPC .............. *G06T 15/08* (2013.01); *G06T 17/00* (2013.01); *G06Q 50/22* (2013.01)

(58) Field of Classification Search
None
See application file for complete search history.

(56) References Cited

U.S. PATENT DOCUMENTS

| 5,891,030 A * | 4/1999 | Johnson | A61B 6/032 600/407 |
| 2005/0245803 A1 * | 11/2005 | Glenn, Jr. | A61B 5/4255 600/407 |
| 2007/0249910 A1 * | 10/2007 | Kiraly | G06T 7/60 600/300 |
| 2008/0044069 A1 * | 2/2008 | DuGal | G06F 19/321 382/128 |
| 2008/0049991 A1 * | 2/2008 | Gering | G06T 19/00 382/128 |
| 2010/0214283 A1 * | 8/2010 | Lobregt | G06T 15/08 345/419 |

(Continued)

OTHER PUBLICATIONS

Truong et al., "Fast and accurate tract unfolding based on stable volumetric image deformation," Mar. 2006, Proceedings vol. 6143, Medical Imaging 2006: Physiology, Function, and Structure from Medical Images, pp. 614317/1-614317/12 (Year: 2006).*

(Continued)

*Primary Examiner* — Andrew G Yang

(57) ABSTRACT

The present embodiments relate to cinematic volume renderings and/or volumetric Monte-Carlo path tracing. By way of introduction, the present embodiments described below include apparatuses and methods for cinematic rendering of unfolded three-dimensional volumes. An image analysis algorithm is performed on an input volume to extract one or more structures of interest, such as a rib centerline, a liver surface or another three-dimensional volume. Based on the extracted three-dimensional structure(s), a geometric transformation is computed to generate an unfolded three-dimensional volume of the structure(s). Cinematic volume rendering techniques are used to generate a rendered image from the unfolded three-dimensional volume.

18 Claims, 4 Drawing Sheets

(56) References Cited

U.S. PATENT DOCUMENTS

| | | | | |
|---|---|---|---|---|
| 2012/0069017 A1* | 3/2012 | Zheng | ............... | G06T 17/20 |
| | | | | 345/420 |
| 2012/0120074 A1* | 5/2012 | Huysmans | ............ | G06T 17/20 |
| | | | | 345/420 |
| 2012/0179193 A1* | 7/2012 | Cohn | ............... | A61L 31/06 |
| | | | | 606/198 |
| 2013/0070996 A1* | 3/2013 | Liu | ............... | G06K 9/00 |
| | | | | 382/131 |
| 2015/0093008 A1* | 4/2015 | Kaftan | ............... | G06T 7/344 |
| | | | | 382/131 |
| 2016/0310101 A1* | 10/2016 | Lee | ............... | A61B 8/085 |
| 2016/0343161 A1* | 11/2016 | Paladini | ............ | G06T 15/08 |
| 2018/0315191 A1* | 11/2018 | Meng | ............... | G06T 3/00 |

OTHER PUBLICATIONS

Kroes, T., Post, F., Botha, C., "Exposure Render: An Interactive Photo-Realistic Volume Rendering Framework", pp. 1-10, vol. 7 No. 7, Jul. 2012.

Ropinski, T., Döring, C., Rezk-Salama, C., "Interactive Volumetric Lighting Simulating Scattering and Shadowing", pp. 169-176, Mar. 2010.

Rezk-Salama, C., "GPU-Based Monte-Carlo Volume Raycasting" Computer Graphics Group, University of Siegen, Germany, pp. 411-414, 2007.

* cited by examiner

CINEMATIC RENDERING OF UNFOLDED 3D VOLUMES

BACKGROUND

Cinematic volume rendering, or volumetric Monte-Carlo path tracing, is the next-generation volume rendering technology based on path tracing. Rather than integrating observations of a ray (i.e., ray casting), cinematic volume rendering is based on path tracing that integrates all illuminance arriving to a single point on the surface of an object. The integrated illuminance is then reduced by a surface reflectance function in order to determine how much of the illuminance will travel to the viewpoint camera. Cinematic volume rendering also integrates over all other data points inside the volume (i.e., the direction of light may change in areas without an implicit surface due to scattering). The integration procedure is repeated for every pixel in the output image. By utilizing cinematic volume rendering, noise is largely suppressed and the structures of the volume renderings are greatly enhanced. Cinematic volume rendering and volumetric Monte-Carlo path tracing are described in PCT/EP2014/070231. FIGS. 1A and 1B illustrate example volume renderings from the same data generated by conventional volume rendering techniques (i.e., ray casting) and by cinematic volume rendering techniques (i.e., path tracing), respectively.

Diagnostic reading of rendered three-dimensional images is time-consuming and error-prone. For example, current clinical practices may require manual and sequential reading of multi-planar reformatting or multi-planar reconstruction (MPR) planes, slice-by-slice and one section at a time. Further, challenges arise from reading rendered three-dimensional images of bones and other anatomic structures because of complex and twisted geometries of the structures and because of variable intensities of diagnostic values across different patients and from different pathologies (e.g., bone intensity, such as bone marrow).

SUMMARY

The present embodiments relate to cinematic volume renderings and/or volumetric Monte-Carlo path tracing. By way of introduction, the present embodiments described below include apparatuses and methods for cinematic rendering of unfolded three-dimensional volumes. An image analysis algorithm extracts one or more structures of interest, such as a rib centerline, a liver surface or another three-dimensional volume, from an input volume. Based on the extracted three-dimensional structure(s), a geometric transformation is performed to generate an unfolded three-dimensional volume of the extracted structure(s). Cinematic volume rendering techniques are performed to generate a rendered image from the unfolded three-dimensional volume.

In a first aspect, a method for generating a volume rendering in a medical system is provided. The method includes receiving three-dimensional scan data of a volume and identifying at least one three-dimensional structure from the three-dimensional scan data by an image processor of the medical system. The image processor unfolds the at least one three-dimensional structure and renders the at least one unfolded three-dimensional structure on a display using volumetric Monte-Carlo path tracing.

In a second aspect, another method for generating a volume rendering in a medical system is provided. The method includes receiving a plurality of voxels representing a plurality of volumes, each voxel having three-dimensional coordinates, extracting the plurality of three-dimensional volumes from the voxels, unfolding the plurality of three-dimensional volumes and rendering the unfolded three-dimensional volumes on a display.

In a third aspect, a system for generating a volume rendering is provided. A scanner is configured to capture an input volume of a patient. A renderer is configured to receive the input volume from the scanner, extract an anatomical structure from the input volume, spatially transform the anatomical structure to a flattened representation, the flattened representation being along a slab thinner in one dimension than the anatomical structure as represented in the input volume, and generate a volume rendering of the unfolded anatomical structure using volumetric path tracing. A workstation is configured to receive the generated volume rendering from the renderer and display the generated volume rendering.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EXEMPLARY EMBODIMENTS

The present embodiments generate a cinematic volume rendering of an unfolded three-dimensional volume. Based on an input volume, an image analysis system extracts one or more structures of interest, such as a rib centerline, a liver surface or another structure. Based on the extracted structures, a geometric transformation is computed to generate an unfolded three-dimensional volume of the extracted structures. Cinematic volume rendering techniques are then used to generate a three-dimensional rendered image from the unfolded three-dimensional volume.

Generating cinematic volume renderings of unfolded three-dimensional volumes may enhance image quality of volume renderings, and may enable new use applications for the volume renderings. For example, an unfolded three-dimensional volume rendering may provide an information summary to a radiologist or other user, allowing for multiple structures to be displayed at the same, decreasing the reading time. Further, a realistic volume rendering of the unfolded three-dimensional volume provides the user with additional confidence in diagnosis and improved conspicuousness during the evaluation and diagnosis. The structure of the scanned patient is presented in a way that may be diagnostically useful where a rendering of the volume without the transformation is not.

Figure 1A:
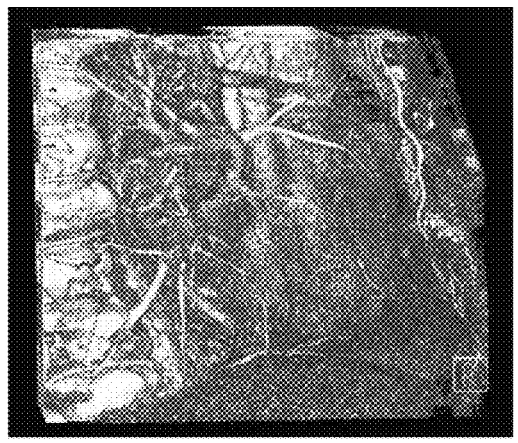
FIG. 1A illustrates an example of a conventional volume rendering.
Figure 1B:
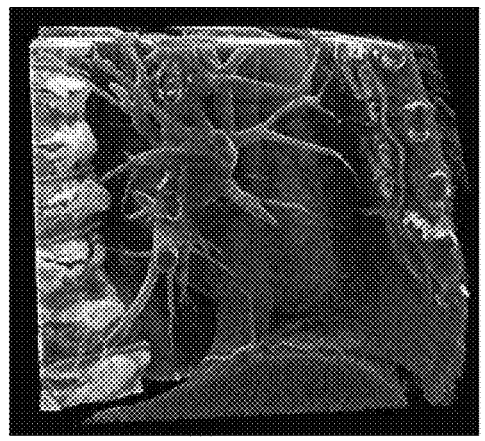
FIG. 1B illustrates an example of a cinematic volume rendering.
Figure 2:
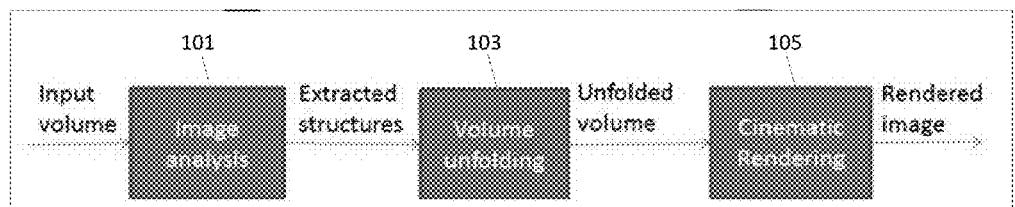
FIG. 2 illustrates a flowchart diagram of an embodiment of a method for cinematic volume rendering of unfolded three-dimensional volumes.

FIG. 2 illustrates a flowchart diagram of an embodiment of a method for cinematic volume rendering of unfolded three-dimensional volumes. The method is implemented by the system of FIG. 7 (discussed below) and/or a different system. Additional, different or fewer acts may be provided. For example, acts 101 and 103 may include multiple sub-acts, or may be performed by a separate system. The method is provided in the order shown. Other orders may be provided and/or acts may be repeated. For example, act 101 may be repeated to extract additional structures, and act 103 may be repeated to unfold additional extracted structures.

At act 101, image analysis is performed on a received input volume. Three-dimensional scan data of the input volume is received by a server or workstation over a network. The volume is scan data representing a patient. The scan data may be received as acquired by the scanner or is loaded as a previously acquired volume from memory.

The server or workstation performs imaging processing on the three-dimensional scan data to identify and extract one or more three-dimensional structures of the input volume from the three-dimensional scan data. Any segmentation may be used. Thresholding, region growing, random walker, pattern matching, machine-learnt classification, or other identification of structure represented in the volume is performed.

The extracted three-dimensional structure(s) may include any three-dimensional structures represented by the three-dimensional scan data (e.g., one or more multiplane three-dimensional structures). Additional image processing may be performed.

In an embodiment, the extracted three-dimensional structures include at least a portion of a patient's skeleton. For example, a portion of the patent's skeleton may include a rib centerline and a vertebra disk localization. Alternatively, other portions of a patient's skeleton may be extracted, such the pelvis, skull or a joint, or the patient's entire skeletal system may be extracted. In another embodiment, the extracted three-dimensional structures include at least a portion of a patient's organ. For example, a portion of the patient's organ may include the patient's liver, heart, lungs, kidneys or other organs. Alternatively, the patent's entire organ system may be extracted. The entire three-dimensional structure may be extracted, the surface of the three-dimensional structure may be extracted, or a combination thereof. In an example, the patient's liver surface, and/or liver surface characteristics, may be extracted.

At act 103, the extracted three-dimensional structure[s] are unfolded. The server or workstation unfolds the extracted three-dimensional structure[s]. A geometric transformation is computed to unfold the three-dimensional structures. Instead of computing a two-dimensional plane through an extracted three-dimensional structure (i.e., one slice), the geometric transformation is computed to model the entire three-dimensional structure[s]. For example, the extracted three-dimensional structure(s) are transformed from a complex and twisted three-dimensional geometry into an unfolded, planar three-dimensional geometry. The unfolding takes a volumetric form as well as flattens the structures. The transform straightens a curved structure such that the three-dimensional geometry is in a plane or slab less thick than occurring in the volume.

In an embodiment, a transformation is performed on the extracted ribs and spine of a patient. In this embodiment, the patent's ribs are untwisted and unfolded into a single plane, and the patient's spine is straightened, resulting in an unfolded model of the patient's rib centerline. Unfolding may include untwisting without straightening or vice versa.

In another embodiment, a transformation is performed on the extracted rib centerline of a patient. Based on the extracted centerline, a cross-section orthogonal to the rib centerline is formed at each rib centerline point. Each rib is typically elliptically shaped. From the obtained rib segmentation result, the "elliptical" shape of each rib is obtained and then the long axis of each rib is computed, as a so-called up-vector. Because the ribs are curved and twisted in three-dimensions (e.g., elliptical), the rib unfolding generates a two-dimensional model from a three-dimensional volume by simultaneously "uncurving" and "untwisting" the ribs purely geometrically (i.e., unfolding). The "uncurving" operation extends a curved rib centerline into a straight line. The second "untwisting" operation follows the up-vector for each rib centerline point while "untwisting" the rib along its centerline. The "uncurving" and "untwisting" operations are performed in three-dimensions.

In another embodiment, the transformation is performed on an extracted organ of a patient. In this embodiment, the three-dimensional surface of the patient's organ is aligned in a planar model (e.g., liver surface). In this embodiment, the surface of the patent's liver is unfolded and flattened. In the aforementioned embodiments, the three-dimensional characteristics of the extracted volumes are maintained in the unfolded three-dimensional volume, such as maintaining the surface texture or response. The geometry, such as edges of the structure, are maintained, but in a straightened or flattened state due to the transform.

In another embodiment, one or more anatomical structures extracted from an input volume are spatially transformed into a flattened representation or model of the anatomical structures. The flattened representation is disposed along a slab that is thinner in one dimension than the anatomical structures as they are represented in the input volume.

In act 105, the unfolded three-dimensional structure(s) are cinematically rendered. The server or workstation performs the cinematic volume rendering. As discussed above, cinematic volume rendering is a rendering technique that generates realistic three-dimensional images. The cinematic rendering is performed using volumetric path tracing, such as volumetric Monte-Carlo path tracing. Rather than integrating observations from a three-dimensional volume on a ray, cinematic volume rendering is performed by integrating over all of the illuminance arriving at a single point on the surface of the object. For example, photon scattering, absorption, and/or reflectance along paths of travel are modeled. Monte Carlo processes are used to converge a large number of modeled photons at a value of illuminance at that point. This illuminance is then reduced by a surface reflectance function to determine the illuminance towards the viewpoint camera. This integration procedure is repeated for every pixel in the output two-dimensional projected image.

Figure 3:
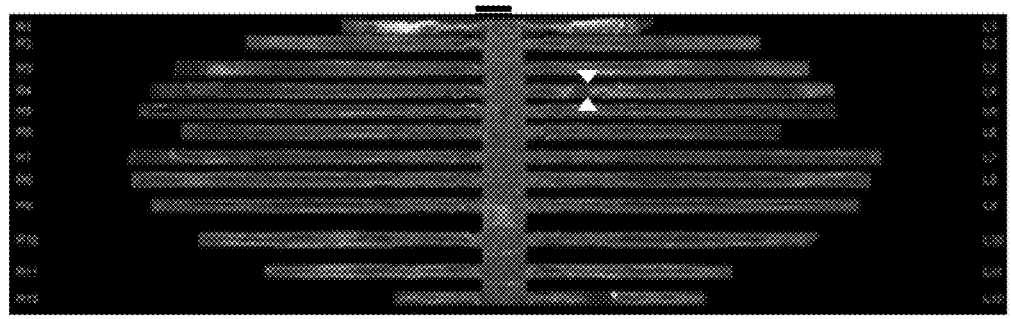
FIG. 3 illustrates an example of a rendering of an unfolded two-dimensional slice of a volume.
Figure 4:
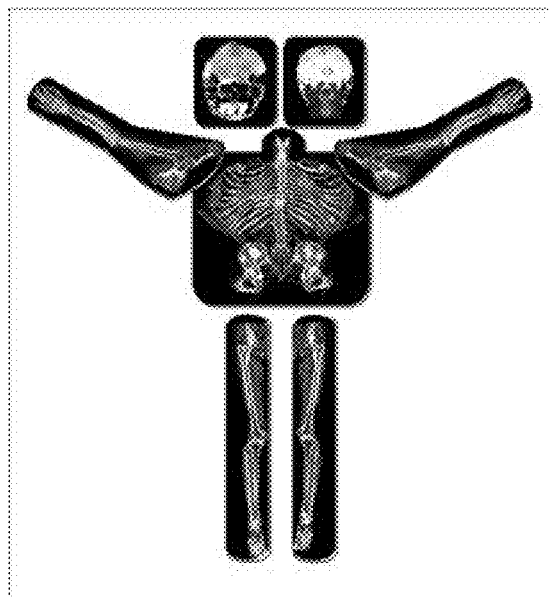
FIG. 4 illustrates another example of a rendering of an unfolded two-dimensional slice of a volume.

FIG. 3 illustrates an example of a rendering of an unfolded two-dimensional slice of a volume. As depicted in FIG. 3, a rib centerline extraction and vertebra disk localization is performed on a single slice to render all 24 ribs in a single plane. Rendering a slice of each rib on a single plane may allow a physician or other user to quickly discover potential clinical findings. For example, as depicted in FIG. 3, extensive rib osteolysis may be identified easily (i.e., demarcated between the triangular markers). FIG. 4 illustrates another example of a rendering of an unfolded two-dimensional slice of a volume. As depicted in FIG. 4, a single slice of the entire skeleton of a patient is rendered after transformation to the slice. In a clinical evaluation, a rendered unfolded two-dimensional view of a patient's ribs shortened radiologists' reading time by 50% and increased the sensitivity of rib fracture detection by 10%. Additional clinical benefits may be realized by rendering an unfolded three-dimensional volume.

Figure 5:
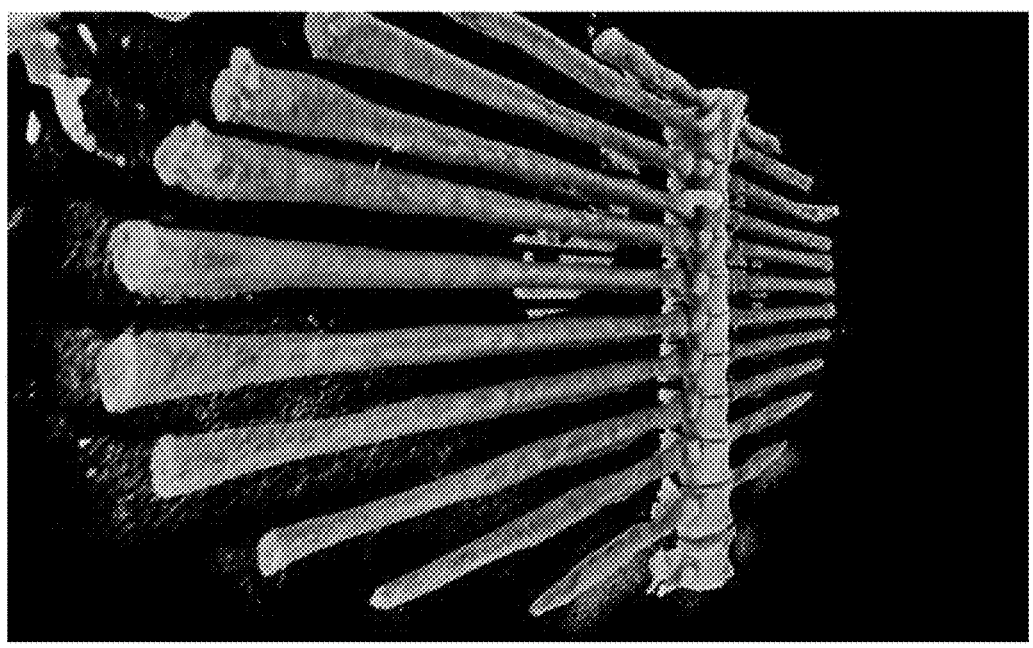
FIG. 5 illustrates an example of a volumetric rendering of an unfolded three-dimensional volume.

FIG. 5 illustrates an example of a cinematic volumetric rendering of an unfolded three-dimensional volume. As depicted in FIG. 5, the extracted and unfolded ribs and spine of a patient are rendered cinematically to generate a three-dimensional volume rendering. Rather than rendering a two-dimensional slice as discussed above and as depicted in FIGS. 3 and 4, a three-dimensional volume rendering, as depicted in FIG. 5, is performed on the unfolded three-dimensional structures to render the patient's ribs and spine in a planar three-dimensional volume rendering. The three-dimensional volume rendering is then displayed providing much greater detail to a physician or other user. Further, as depicted in FIG. 5, the surface characteristics of the unfolded three-dimensional structures is rendered with clarity. FIG. 5 has a perspective view of the unfolded volume. Any view direction may be used.

Rendering unfolded three-dimensional structures allow the rendered images to include multiple structures in the same rendering, resulting in more information available to the user compared to a rendered image based on a computed two-dimensional plane. Further, cinematic volume rendered images that are based on the unfolded three-dimensional structures allow for realistic images of multiple structures in the same rendering, resulting in greater clarity in the rendered images and increased conspicuousness during diagnosis.

Figure 6:
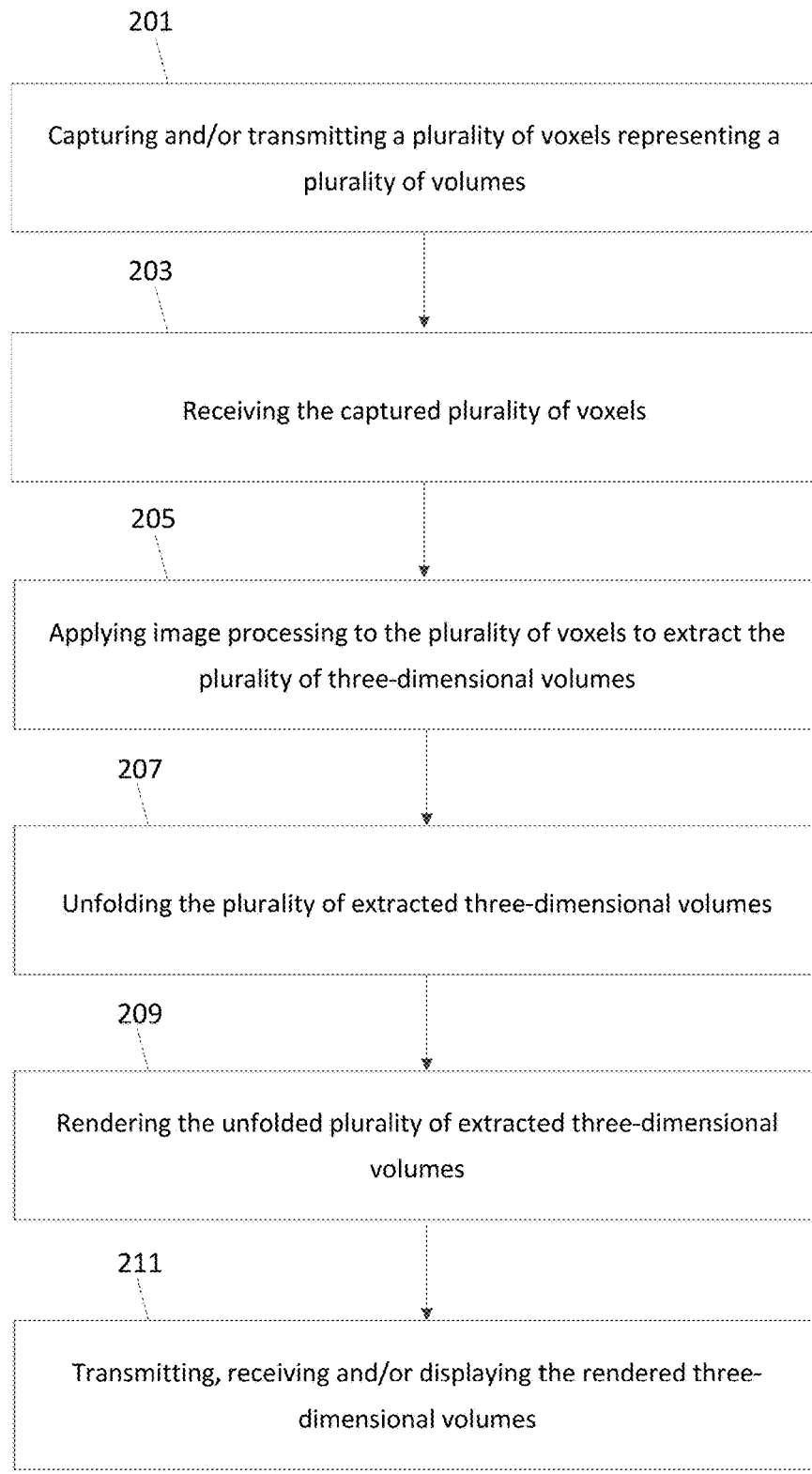
FIG. 6 illustrates another flowchart diagram of an embodiment of a method for cinematic volume rendering of unfolded three-dimensional volumes.

FIG. 6 illustrates another flowchart diagram of an embodiment of a method for cinematic volume rendering of unfolded three-dimensional volumes. The method is implemented by the system of FIG. 7 (discussed below) and/or a different system. Additional, different or fewer acts may be provided. For example, acts 201 and 203 may be omitted or performed by a separate systems. The method is provided in the order shown. Other orders may be provided and/or acts may be repeated. For example, acts 205 and 207 may be repeated to extract and unfold additional volumes. Further, the acts may be performed concurrently as parallel acts. For example, acts 205 and 207 may be performed concurrently to extract and unfold different volumes simultaneously.

At act 201, one or more volumes are scanned to capture a plurality of voxels representing a plurality of volumes (i.e., scan data). The plurality of voxels make up a three-dimensional data set for the scanned volumes, and may be captured using computerized tomography (CT), magnetic resonance (MR) imaging, ultrasound, emission tomography, or another scanning modality. For example, each voxel is represented by three-dimensional voxel coordinates (x, y, z) and an image intensity (i). The captured three-dimensional volumes may include any three-dimensional volumes (e.g., one or more multiplane three-dimensional structures), such as a portion or the entirety of a patient's skeleton, one or more of the patient's organs, other anatomical structures, or a combination thereof. The plurality of voxels are captured by a scanner and transmitted to a server or a workstation over a network. At act 203, the plurality of voxels are received by the server or workstation over the network.

At act 205, image processing is applied to the plurality of voxels to extract a plurality of three-dimensional volumes. Segmentation is performed to identify voxels belonging to or representing the specific structure or structures. Any number of separate volumes (e.g., one for each structure segmented from the scan voxels) may be created. Additional image processing may also be performed.

At act 207, the extracted three-dimensional volumes are unfolded. Geometric transformations are applied to the voxels representing each of the extracted plurality of three-dimensional volumes. For example, due to complex and twisted geometries, the extracted three-dimensional volumes, or parts thereof, may be in different planes (i.e., multi-planar structures). The extracted three-dimensional volumes are unfolded and aligned to be in the same plane, and the unfolding may involve untwisting each of the plurality of volumes. Further, a plurality of interconnected structures may be arranged on the same plane while maintaining the interconnections between the structures. For example, when a patient's ribs are unfolded, the interconnections between each rib and the spine may be maintained. In another example, when a patient's organs are unfolded, such as a patients lungs, the interconnectivity between the organs (e.g., the right and left lung) are maintained.

At act 209, a cinematic volume rendering is generated from the unfolded three-dimensional volumes. For example, FIG. 5 depicts an example of a volumetric rendering of an unfolded three-dimensional volume. At act 211, the generated volume rendering is transmitted by the server and received by the workstation. The workstation displays the generated volume rendering. Alternatively, the workstation performs acts 205, 207 and 209, and displays the generated volume rendering at a display for the workstation.

Figure 7:
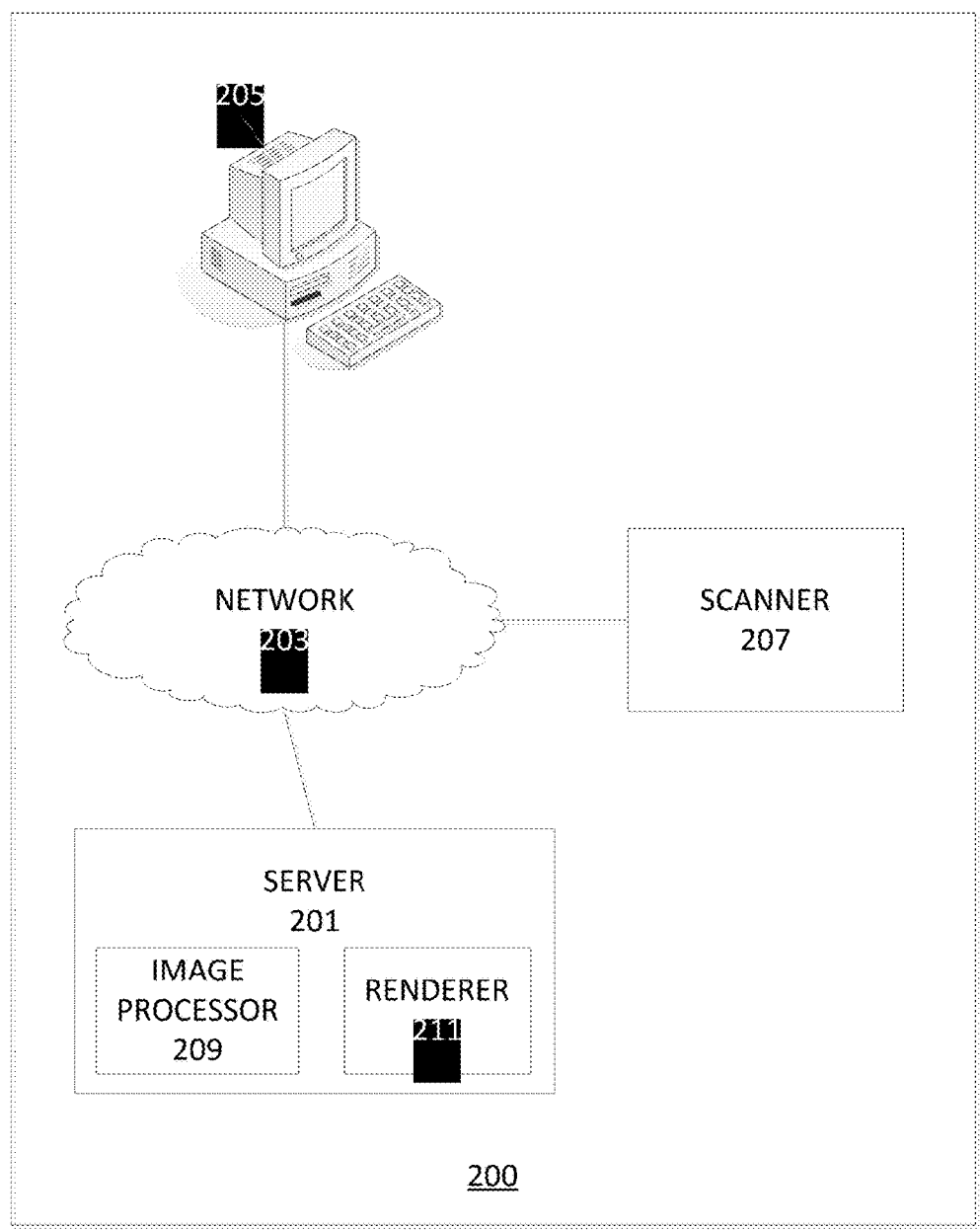
FIG. 7 illustrates an embodiment of a system for cinematic volume rendering of unfolded three-dimensional volumes.

FIG. 7 illustrates an embodiment of a medical system 200 for generating a cinematic volume rendering of unfolded three-dimensional volumes. The medical system 200 includes a server 201, a network 203, a workstation 205 and a scanner 207. Additional, different, or fewer components may be provided. For example, additional servers 201, networks 203, workstations 205 and/or scanners 207 are used. In another example, the servers 201 and the workstation 205 are directly connected, or implemented on a single computing device. In yet another example, the server 201, the workstation 205 and the scanner 207 are implemented on a single scanning device. As another example, the workstation 205 is part of the scanner 207. In yet another embodiment, the medical scanner 207 performs the extraction, transformation and rendering without use of the network 203, server 201, or workstation 205.

The scanner 207 is configured to capture scan data of a volume for use as an input volume. The scanner 207 is a three-dimensional scanner, such as a computerized tomography (CT), ultrasound, x-ray, or magnetic resonance (MR) scanner. Other scanners may be used.

The network 203 is a wired or wireless network, or a combination thereof. Network 203 is configured as a local area network (LAN), wide area network (WAN), intranet, Internet or other now known or later developed network configurations. Any network or combination of networks for communicating between the client computer 205, the scanner 207, the server 201 and other components may be used.

The server 201 is a server computer platform having hardware such as one or more central processing units (CPU), a system memory, a random access memory (RAM) and input/output (I/O) interface(s). The server 201 also includes a graphics processor unit (GPU) to accelerate image rendering. The server 201 is implemented on one or more server computers connected to network 203. Additional, different or fewer components may be provided.

The server 201 is configured to execute an application to receive an input volume from the scanner 207 over the network 203. The server 201 is further configured to execute an application (e.g., an image processing module or image processing engine) to perform image processing to the input volume, such as to extract one or more structures from the input volume. The server 201 is further configured to execute an application (e.g., another image processing module, such as an unfolding module, or another image processing engine) to unfold the extracted structures. The server 201 is further configured to execute an application (e.g., a cinematic rendering module or rendering engine) to generate a cinematic volume rendering of the unfolded structures using volumetric Monte-Carlo path tracing. The server 201 is also configured to transmit the generated volume rendering to the workstation 205 over the network 203. In an embodiment, the server 201 includes image processor 209 and renderer 211. The image processor 209 and renderer 211 may be implemented in the same or separate hardware or devices. In another alternative, the image processor and/or renderer 211 may be part of the workstation 205 or the scanner 207. In other alternative embodiments, the extraction, rendering, and/or transmission are performed by separate processors or devices.

The system 200 includes a workstation 205. The workstation 205 is configured to execute an application to receive the generated volume rendering from the server 201 over the network 203. The workstation is further configured to execute an application to display the generated volume rendering. Alternatively or additionally, the scanner 207 receives and displays the volume rendering.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

We claim:

1. A method for generating a volume rendering in a medical system, the method comprising:
receiving, by an image processor of the medical system, three-dimensional scan data of a volume;
identifying, by the image processor, at least one three-dimensional structure from the three-dimensional scan data, the at least one three-dimensional structure being a branching structure having multiple interconnected parts;
unfolding, by the image processor, the at least one three-dimensional structure into at least one unfolded three-dimensional structure, the at least one unfolded three-dimensional structure being an unfolded branching structure having been both straightened and untwisted in three dimensions, wherein the unfolding comprises maintaining interconnections of the interconnected parts; and
rendering, by the image processor on a display, the at least one unfolded three-dimensional structure, the rendering comprising volumetric Monte-Carlo path tracing.

2. The method of claim 1 wherein identifying comprises extracting at least one three-dimensional structure from the scan data.

3. The method of claim 2 wherein extracting the at least one structure comprises extracting at least a portion of a skeleton of a patient.

4. The method of claim 2 wherein extracting the at least one structure comprises extracting at least a portion of an organ of a patient.

5. The method of claim 4 wherein extracting the at least one structure comprises extracting at least a portion of a surface of the organ of a patient.

6. The method of claim 1 wherein the at least one three-dimensional structure comprises a plurality of three-dimensional structures in different planes, and
wherein the unfolding comprises transforming each of the plurality of three-dimensional structures into a plane.

7. The method of claim 6 wherein the transforming comprises a geometric transformation.

8. The method of claim 6 wherein the transforming comprises a geometric transformation.

9. The method of claim 1 wherein the unfolding comprises aligning the surface of the at least one structure in a plane.

10. A method for generating a volume rendering in a medical system, the method comprising:
receiving a plurality of voxels representing a plurality of volumes, wherein each voxel has three-dimensional coordinates;
extracting the plurality of three-dimensional volumes from the voxels, at least one of the plurality of three-dimensional volumes being a branching structure having multiple parts;
unfolding the plurality of three-dimensional volumes into a plurality of unfolded three-dimensional volumes, at least one of the plurality of unfolded three-dimensional volumes being an unfolded branching structure having centerlines straightened on a plane and maintained three-dimensional geometry in a volumetric form of the three-dimensional volumes untwisted relative to the centerlines, wherein the extracted plurality of three-dimensional volumes comprise a plurality of interconnected structures, wherein the unfolding comprises arranging each of the plurality of interconnected structures on the plane and wherein the arranging maintains interconnections between the plurality of interconnected structures; and
rendering the unfolded three-dimensional volumes on a display.

11. The method of claim 10 wherein the unfolding comprises applying geometric transformations to the voxels representing each of the extracted plurality of three-dimensional volumes.

12. The method of claim 10 wherein the extracted plurality of three-dimensional volumes comprise a plurality multi-planar structures, and wherein the unfolding comprises aligning each of the plurality multi-planar structures in a plane.

13. The method of claim 10 wherein the extracted plurality of three-dimensional volumes comprise a plurality twisted structures, and wherein the unfolding comprises untwisting each of the plurality twisted structures relative to the centerlines.

14. The method of claim 10 wherein the rendering comprises volumetric path tracing.

15. The method of claim 14, wherein the rendering comprises volumetric Monte-Carlo path tracing.

16. The method of claim 15, further comprising:
displaying the rendering of the unfolded three-dimensional volumes.

17. A system for generating a volume rendering, the system comprising:
a scanner configured to capture an input volume of a patient; and
a renderer configured to:
receive, from the scanner, the input volume;
extract an anatomical structure from the input volume, the anatomical structure being a branching structure having multiple connected parts, at least one of the connected parts being twisted and curved;
spatially transform the anatomical structure to a flattened representation, the flattened representation being along a three-dimensional slab thinner in one dimension than the anatomical structure as represented in the input volume, the flattened representation being an unfolded branching structure with the multiple connected parts as unfolded being connected, the at least one of the connected parts as unfolded being both straightened and untwisted in three dimensions; and
generate, using volumetric path tracing, a volume rendering of the unfolded anatomical structure.

18. The system of claim 17 further comprising:
a workstation configured to:
receive, from the renderer, the generated volume rendering; and
display the generated volume rendering.

* * * * *